(12) United States Patent
Tortola

(10) Patent No.: US 12,048,418 B2
(45) Date of Patent: Jul. 30, 2024

(54) MULTI-ANGLE IMAGING PLATFORM

(71) Applicant: VTI Medical, Inc., Waltham, MA (US)

(72) Inventor: Angelo Tortola, Lexington, MA (US)

(73) Assignee: VTI Medical, Inc., Waltham, MA (US)

( * ) Notice: Subject to any disclaimer, the term of this patent is extended or adjusted under 35 U.S.C. 154(b) by 356 days.

(21) Appl. No.: 17/197,720

(22) Filed: Mar. 10, 2021

(65) Prior Publication Data

US 2021/0282628 A1    Sep. 16, 2021

Related U.S. Application Data

(60) Provisional application No. 62/987,631, filed on Mar. 10, 2020.

(51) Int. Cl.
*A61B 1/00* (2006.01)
*A61B 1/04* (2006.01)
(Continued)

(52) U.S. Cl.
CPC ...... *A61B 1/00183* (2013.01); *A61B 1/00045* (2013.01); *A61B 1/00066* (2013.01);
(Continued)

(58) Field of Classification Search
CPC ............ A61B 1/00183; A61B 1/00045; A61B 1/00066; A61B 1/00137; A61B 1/04; A61B 1/0669; A61B 1/0684; A61B 1/07; A61B 8/12; A61B 8/4416; A61B 1/05; A61B 1/0676
See application file for complete search history.

(56) References Cited

U.S. PATENT DOCUMENTS 6,325,760 B1 *  12/2001  Takanori .................. A61B 8/14
                                                          600/459
6,398,725 B1     6/2002  Thompson
(Continued)

FOREIGN PATENT DOCUMENTS

EP    2502572 A2    9/2012
EP    2514370 A2   10/2012
(Continued)

OTHER PUBLICATIONS

International Search Report and Written Opinion received for PCT/US2021/021691. Mail date: Jun. 18, 2021. 14 pages.

*Primary Examiner* — Joseph M Santos Rodriguez
*Assistant Examiner* — Kaitlyn E Sebastian
(74) *Attorney, Agent, or Firm* — Finch & Maloney PLLC

(57) ABSTRACT

A system and method are provided for controlling achieving fine angle control within small diameter devices. An imaging device is provided with a multi-angle imaging platform. In some embodiments, a flexible printed circuit board (PCB) is provided with conductors and a camera angle activator pivot for rotating the camera head. In some embodiments, a ball and socket joint is used to rotate the camera head within a distal end of the elongate shaft. In some embodiments, a spring mechanism is used to rotate the camera head within a distal end of the elongate shaft. In some embodiments, the viewing angle of the imaging device is adjusted via movement of an inner tube with respect to an outer tube and corresponding adjustment of the flexible PCB, ball and socket joint, and/or spring mechanism.

20 Claims, 10 Drawing Sheets

(51) Int. Cl.
  *A61B 1/06* (2006.01)
  *A61B 1/07* (2006.01)
  *A61B 8/00* (2006.01)
  *A61B 8/12* (2006.01)

(52) U.S. Cl.
  CPC ............ *A61B 1/00137* (2013.01); *A61B 1/04* (2013.01); *A61B 1/0669* (2013.01); *A61B 1/0684* (2013.01); *A61B 1/07* (2013.01); *A61B 8/12* (2013.01); *A61B 8/4416* (2013.01)

(56) References Cited

U.S. PATENT DOCUMENTS

| | | | |
|---|---|---|---|
| 6,428,470 | B1 | 8/2002 | Thompson |
| 9,649,016 | B2 | 5/2017 | Wada et al. |
| 9,681,797 | B2 | 6/2017 | Scherr et al. |
| 10,278,568 | B2 | 5/2019 | Manohara et al. |
| 10,517,470 | B2 | 12/2019 | Hopkins, Jr. |
| 2003/0069565 | A1* | 4/2003 | Miser ............... A61B 17/00234 606/1 |
| 2007/0055103 | A1 | 3/2007 | Hoefig et al. |
| 2012/0308977 | A1* | 12/2012 | Tortola ................. G09B 23/285 434/262 |
| 2014/0221749 | A1 | 8/2014 | Grant et al. |
| 2016/0073855 | A1 | 3/2016 | Farr et al. |
| 2017/0078583 | A1 | 3/2017 | Haggerty et al. |
| 2017/0325671 | A1* | 11/2017 | Hopkins, Jr. ........ A61B 1/0008 |
| 2019/0268581 | A1* | 8/2019 | Miyazaki ............... H04N 23/88 |
| 2019/0328217 | A1 | 10/2019 | Moreau et al. |

FOREIGN PATENT DOCUMENTS

| | | | |
|---|---|---|---|
| EP | 2950702 B1 | 8/2017 | |
| EP | 2765899 B1 | 3/2018 | |
| WO | 03/013349 A2 | 2/2003 | |
| WO | 2011044878 A1 | 4/2011 | |
| WO | 2012101966 A1 | 8/2012 | |
| WO | WO-2012101966 A1 * | 8/2012 | ......... A61B 1/00183 |

* cited by examiner

MULTI-ANGLE IMAGING PLATFORM

CROSS-REFERENCE TO RELATED APPLICATIONS

This application claims benefit of U.S. Provisional Patent Application No. 62/987,631 filed on Mar. 10, 2020, which is herein incorporated by reference in its entirety.

SUMMARY OF THE INVENTION

Embodiments are presented for an articulating multi-angle head configured for use with an imaging device and an elongate shaft for entry into an anatomical region of interest. Advantages provided by the present disclosure include allowing multiple views of an area of interest with a single straight endoscope where the imaging device is configured to internally rotate within the distal tip of the device. The present disclosure provides an improved system configured to provide fiber optic quality images without a fiber optic system, visibility of a large range of viewing angles with a small outside diameter, configured for various uses. The multi-angle imaging platform can be used in a variety of surgical procedures, such as arthroscopic, sinus (ENT), gastroenterological, abdominal, cranial, and/or laparoscopic procedures. The multi-angle imaging platform can be used for arthroscopic evaluation of joints during surgery. The multi-angle imaging platform can be used, for example, in laparoscopic gall bladder surgery. The multi-angle imaging platform can be used in urogynecology applications, such as urinary inspection or inspection of the vaginal cervix, for example. In some embodiments, the multi-angle imaging platform can be used with procedures including use of a surgical robot. In other embodiments, the device can be used in commercial or industrial settings, such as industrial process monitoring, building inspections and concealed video monitoring of human activity.

Some embodiments of the disclosure include use with capsule endoscope applications.

Some embodiments of the disclosure include a multi-angle endoscope, comprising a distal tip including an imaging device and a light pipe surrounding the imaging device, an elongate shaft between the distal tip and a proximal handle end. The proximal handle end comprising a pivot grip configured for rotation of the imaging device about 360° of viewing. The proximal handle end further comprising an adjustable camera pivot arm. In some embodiments, the adjustable camera pivot arm is configured with detents every 15°. In some embodiments, the adjustable camera pivot arm is configured for rotation of the angle of the camera head between 0° and 60°. In some embodiments, the adjustable camera pivot arm is configured for rotation of the angle of the camera head between 0° and 90°. In some embodiments, the adjustable camera pivot arm is configured to pivot with infinite stops. The proximal handle end may further comprise a recording button 160 for initiating detection of an image at a distal end of the device.

In some embodiments, a flexible printed circuit board (PCB) is provided with conductors and a camera angle activator pivot for rotating the camera head. In some embodiments, a ball and socket joint is used to rotate the camera head within a distal end of the elongate shaft. In some embodiments, a spring mechanism is used to rotate the camera head within a distal end of the elongate shaft. In some embodiments, the viewing angle of the imaging device is adjusted via movement of an inner tube with respect to an outer tube and corresponding adjustment of the flexible PCB, ball and socket joint, and/or spring mechanism. In some embodiments, the camera angle activator pivot is a rod positioned horizontally to a longitudinal axis of the elongate shaft and attached at a distal end of an inner barrel configured to anchor one end of a base of the imaging device at it rotates.

In some embodiments, the imaging device may comprise a lens system positioned distally to a camera imager. In some embodiments, the imaging device is a complimentary metal oxide semiconductor (CMOS) camera imager. In some embodiments, the imaging device is an ultrasound probe. In some embodiments, the imaging device comprises one or more LED lights. In some embodiments, one or more LED lights are positioned proximally to a light pipe. In some embodiments, the imaging device may include one or more selected from the group comprising a CMOS camera, an ultrasound probe, and a set of LED lights.

In some embodiments, a light pipe may be configured concentrically around the imaging device.

In some embodiments, the outside diameter of the elongate shaft of the imaging platform may be 10 mm or less, 6 mm or less, or 4 mm or less. In some embodiments, the wall thickness of the elongate shaft is 2 mm or less, 1 mm or less, or 0.5 mm or less. In some embodiments, the outside diameter of a distal tip of the imaging platform may be 10 mm or less, 6 mm or less, or 4 mm or less. In some embodiments, an OmniVision imager or similar imager may be used as the imaging device. The size of the imaging array and overall dimensions of the imager will affect the diameter of the elongate shaft and will depend upon image application (i.e. gastroenterology, laparoscopy, arthroscopy, urology, or ENT, for example). In some embodiments, stereoscopic imaging may be accomplished through use of a second imaging device at a distal end of the elongate shaft.

In some embodiments, the elongate shaft comprises one or more selected from a list comprising plastic and stainless steel. In some embodiments, the elongate shaft terminates at a distal end with an optical dome. In some embodiments, the optical dome is configured about the entirety of a distal end portion to allow for clear visualization of an area of interest proximate to the distal end of the elongate shaft, as the imaging device is rotated according to various embodiments of the disclosure. In some embodiments, the elongate shaft additionally comprises one or more working channels for insertion of auxiliary instruments, such as graspers, suction, aspiration, insufflation, or the like.

In some embodiments, the multi-angle imaging platform is configured to be autoclavable. In some embodiments, the multi-angle imaging platform is configured as a single use, disposable device.

These and other features of the present embodiments will be understood better by reading the following detailed description, taken together with the figures herein described. The accompanying drawings are not intended to be drawn to scale. For purposes of clarity, not every component may be labeled in every drawing.

DETAILED DESCRIPTION

The following description is merely exemplary in nature and is not intended to limit the present disclosure, application, or uses.

Figure 1:
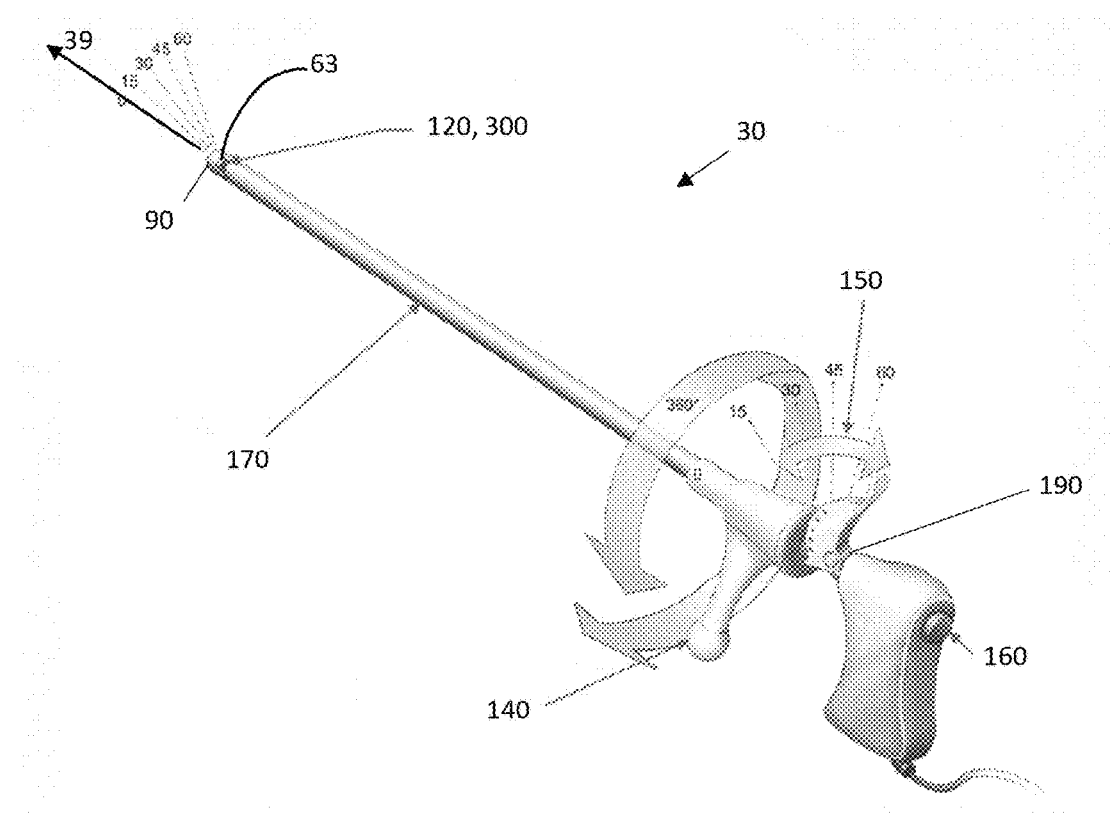
FIG. 1 is a perspective view of a multi-angle imaging device, in accordance with one embodiment of the disclosure.

It is desirable to have a small diameter multi-angle imaging platform configured for a variety of viewing angles in a narrow passageway of an area of interest. Multi-angle imaging platform includes multi-angle imaging device 30 and various embodiments are presented herein for adjusting the viewing angle and barrel angle of a camera or imager positioned at a distal tip of the device. FIG. 1 is a perspective view of multi-angle imaging device 30 comprising imager 120 positioned on multi-angle platform 300 at distal end 90. Pivot lever 150 is positioned at proximal end 190 of multi-angle imaging device and is configured for grasping by a user's hand. Pivot lever 150 is configured to pivot multi-angle imaging platform 300 to vary angle α of viewing axis 75 from between 0°-70°. In some embodiments, pivot lever 150 is configured with detents every 15 degrees for ease of operation. During operation, pivot lever 150 clicks into place at each detent. Pivot handle 140 is configured for grasping by a hand of a user and is positioned at a proximal end 190 of multi-angle imaging device 30. Pivot handle 140 is configured to rotate the viewing angle of distal end about 360° of rotation with a viewing field of about 120° at each rotational position. Pivot handle 140 is rotated to rotate camera 63 or imager 120 about barrel axis 39. The relationship between the movement of pivot handle 140 and the viewing angle can be 1:1, less than 1:1 or greater than 1:1. A higher ratio provides greater movement of the field of view so that, for example, a 120° range of movement of the pivot handle can provide for a 360° movement of the viewing angle. A lower ratio can provide more precise control of the viewing angle. For example, moving the pivot handle 120° can result in a more precise 40° change in the field of view. These different ratios can be achieved, for example, through mechanical connections such as gearing or pulleys or can be altered electronically.

Figures 2A, 2B, 2C:
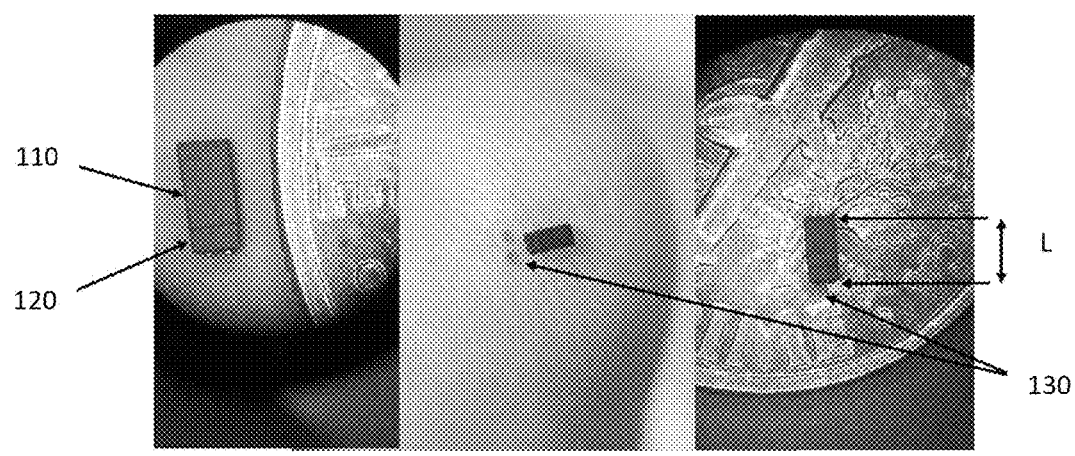
FIG. 2A is a photograph of a camera imager and a lens system for size comparison with a dime, in accordance with one embodiment of the disclosure.
FIG. 2B is a photograph of a camera imager and a lens system for size comparison with a finger, in accordance with one embodiment of the disclosure.
FIG. 2C is a photograph of a camera imager and a lens system for size comparison with a dime, in accordance with one embodiment of the disclosure.

FIGS. 2A-C are photographs of one embodiment of lens system 110, camera imager 120, and light emitting diodes 130 for size comparison to a dime and a fingertip. In some embodiments, a length L of the combination of lens system 110, camera imager 120, and light emitting diodes 130 is between 2 mm and 5 mm, between 2 mm and 3 mm, or between 3 mm and 4 mm.

Figure 3:
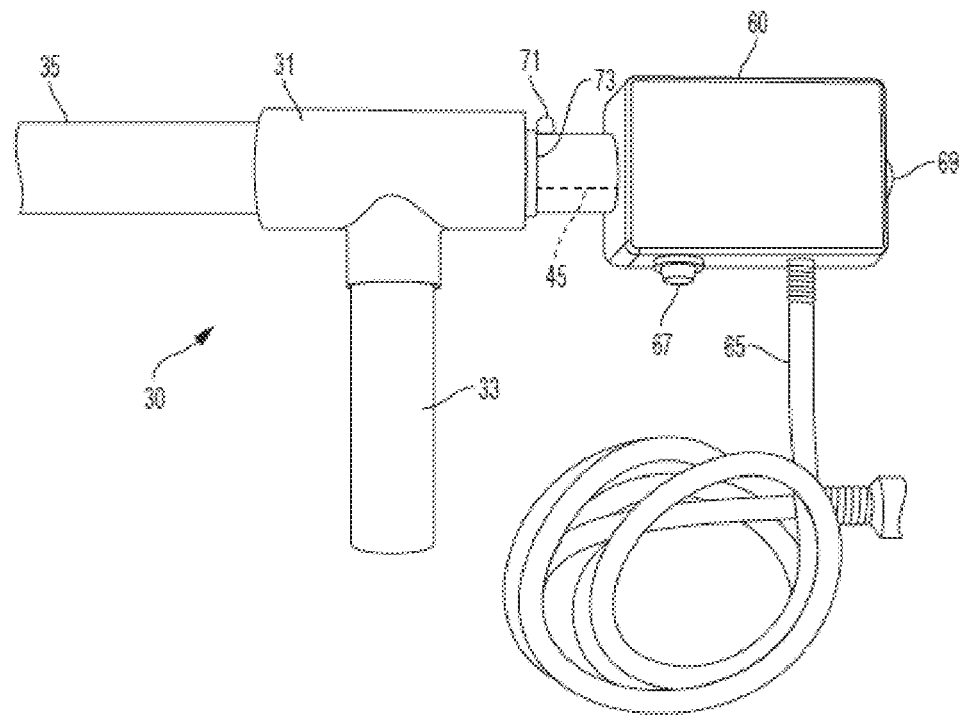
FIG. 3 is a proximal handle portion of a multi-angle imaging device, in accordance with one embodiment of the disclosure.
Figure 4:
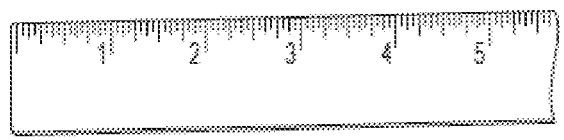
FIG. 4 is a side view of a distal end portion of a multi-angle imaging device, illustrating movement of an inner barrel with respect to an outer barrel, showing the imaging device positioned at an angle of 0° with respect to a longitudinal axis of an elongate shaft, in accordance with one embodiment of the disclosure.
Figure 4:
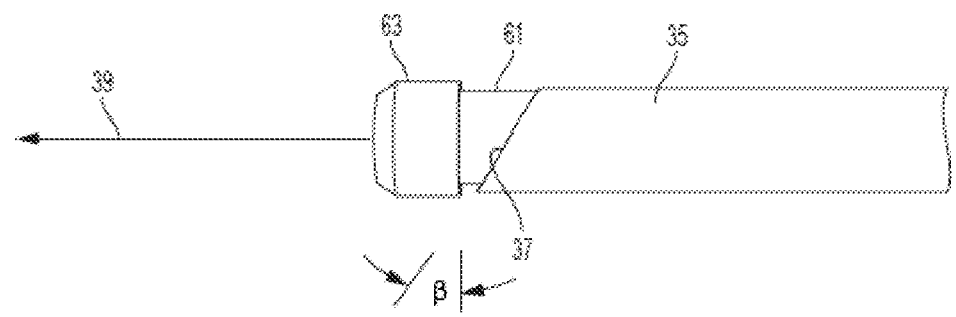
Figure 5:
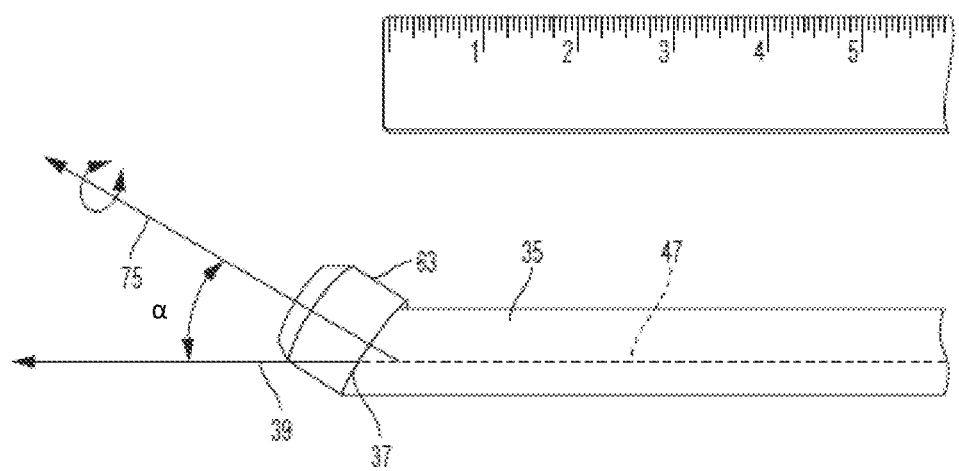
FIG. 5 is a side view of a distal end portion of a multi-angle imaging device, illustrating the imaging device positioned at an angle of 30° with respect to a longitudinal axis of an elongate shaft, in accordance with one embodiment of the disclosure.

The components and operation of one embodiment of the multi-angle imaging device 30 may be described with reference to FIGS. 3 through 5 in which is shown a housing 31 into which a handle 33 and an outer barrel 35 are fitted. The outer barrel 35 has a first end fitted into the housing 31, as shown in FIG. 3, and a second end having a skewed barrel end 37 oriented at about thirty degrees with respect to a barrel axis 39, as best shown in FIG. 4. An inner barrel 61 is slidably retained within the outer barrel 35. As shown, the inner barrel 61 has a longer length than the length of the outer barrel 35.

In the example shown in FIG. 3, a video electronic module 60 is connected to a first end of the inner barrel 61 (not shown). A video camera 63 or imager 120 is connected to a second end of the inner barrel 61 (see, for example, FIGS. 4-6). In some embodiments, an electronic cable 45 runs inside the length of the inner barrel 61 to convey electronic digital image data from the video camera 63 or imager 120 to the video electronic module 60. In some embodiments, electronic digital image data is conveyed along elongate shaft 170 of the multi-angle imaging device 30 via flexible printed circuit board 250. Flexible printed circuit board 250 is configured with conductors 255 which allow for the flow of electrical signals along the length of shaft 170. In some embodiments, output cable 65 may be electrically connected to an output of the electronic module 60 so as to provide an image 13, and optional electronically-generated cross hairs 15, on display device 11 (see FIG. 14). The video electronic module 60 may include switches 67 and 69 to begin a countdown timer (see FIG. 14) and an elapsed-time timer (not shown), for example, for use in a training session.

Figure 14:
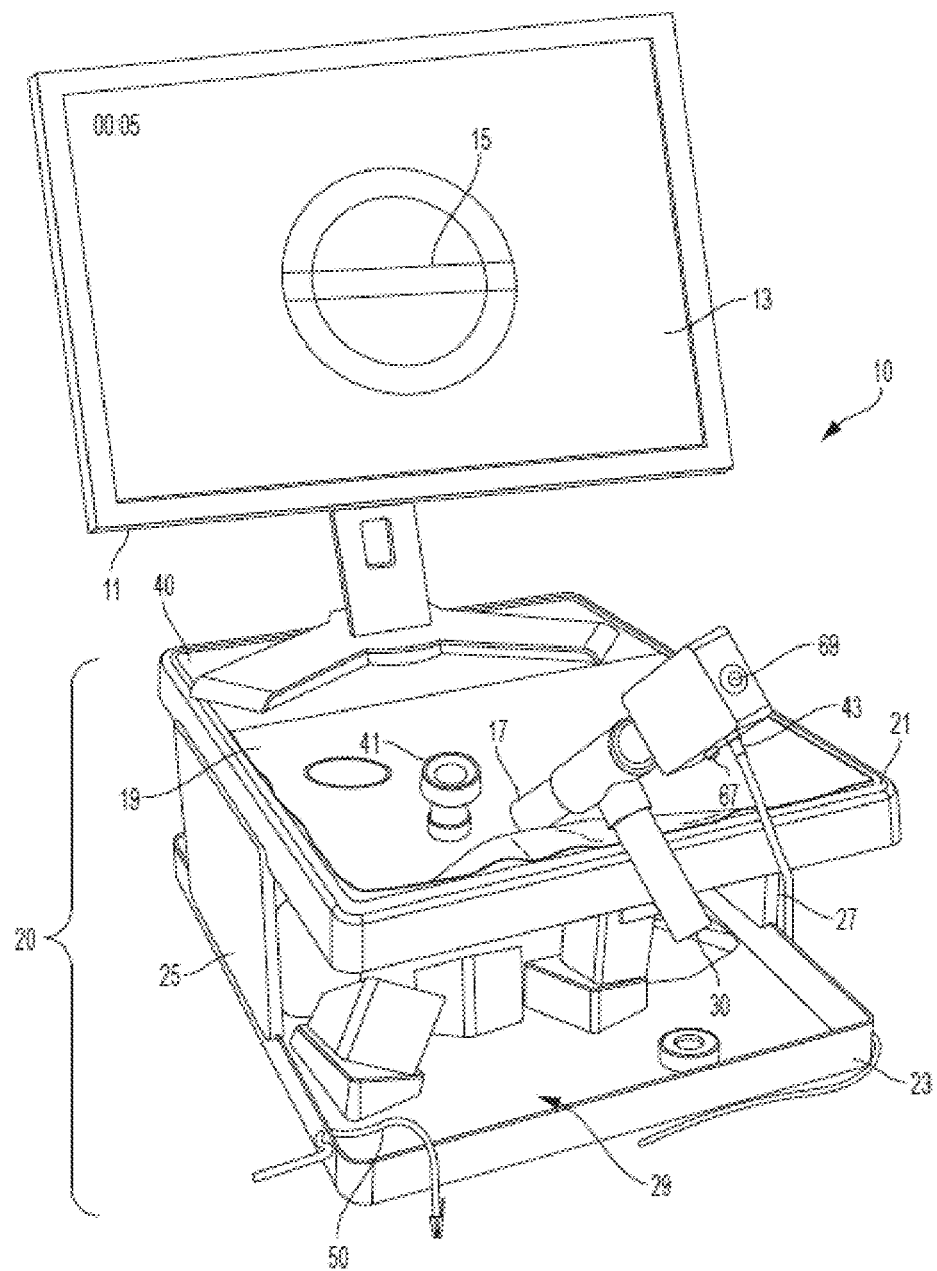
FIG. 14 is an isometric view of the basic elements of a laparoscopic skills training system, in accordance with one embodiment of the disclosure.

In some embodiments, the multi-angle imaging device 30 may be used alongside a tool for laparoscopic training, as shown for example in FIG. 14. Laparoscopic skills training system 10 includes a trainer platform assembly 20 comprising a training platform 21, a base 23, a left side support 25, and a right side support 27, an alligator clip with tether 50, where the trainer platform assembly 20 is secured to the base 23 by the left side support 25 and the right side support 27. A display device 11, such as a laptop or a computer monitor, may be placed on or near the trainer platform assembly 20. The platform surface 40 may further include a left port 41 and a right port 43.

In a first mode of operation of the training module, camera navigation skills are developed. In the first mode of operation, the optical axis of the video camera 63 or imager 120 is generally aligned with barrel axis 39, i.e., the "zero degree axis." In performing a first skill set using the laparoscopic skills training system 10, the user begins by inserting the training endoscope 30 through the simulated skin 19 into the working volume 29 via the endoscope opening 17. In a second mode of operation, shown in FIG. 3, video electronic module 60 is moved away from the endoscope housing 31, causing the inner barrel 61 to move rearward within the outer barrel 35, until a latching button 71 protrudes to engage an end 73 of the viewing barrel 35. This causes the imaging device 63 to pivot in relation to the barrel axis at an angle of α° so as to orient an optical axis of the imaging device along an angled viewing axis 75, shown in FIG. 5. In the embodiments described herein, angle α can vary, for example, from between 0°-70°, 0°-10°, 0°-30°, 0°-45°, 15°-30°, 30°-45°, or 45°-70°. Angle α may be adjusted using pivot lever 150.

FIG. 4 is a side view of a distal end portion of a multi-angle imaging device, illustrating movement of an inner barrel with respect to an outer barrel, showing the imaging device positioned at an angle of 0° with respect to a longitudinal axis of an elongate shaft. FIG. 5 is a side view of a distal end portion of a multi-angle imaging device, illustrating the imaging device positioned at an angle of 30° with respect to a longitudinal axis of an elongate shaft. FIGS. 4-5 illustrate elastic member 47, disposed within the inner barrel 61, is configured and attached to the imaging device 63 such that the imaging device 63 is urged to rotate and to position itself against the skewed barrel end 37 of the outer barrel 35 when the inner barrel 61 has moved rearward within the outer barrel 35. In this embodiment, the angle β of the skewed barrel end 37 has a direct effect on the angle of viewing axis 75. When latching button 71 (shown in FIG. 3) is depressed, inner barrel 61 is free to move forward within outer barrel 35. When inner barrel 61 moves forward within outer barrel 35, imaging device 63 or imager 120 may return to a first mode of operation and the optical axis is again aligned with the barrel axis 39, or zero degree (0°) axis.

Pivot lever 150 can rotate around a pivot point causing linear motion of the inner barrel which in turn causes angular motion of the imaging device. In one embodiment, the angle α of the imaging device 63 can be varied continuously by a user during inspection of an area of interest. In some embodiments, detents are provided within pivot lever 150 for viewing at regular intervals of 5°, 10°, 15°, 20°, or 30° for example. In this embodiment, position indicators (not shown) may be provided on the inner barrel 61 such that the linear sliding movement of the inner barrel within the outer barrel 35 can be adjusted so as to position the imaging device 63 at varying angles, according to which position indicator on the inner barrel remains visible at the end of the outer barrel 35.

Figure 6:
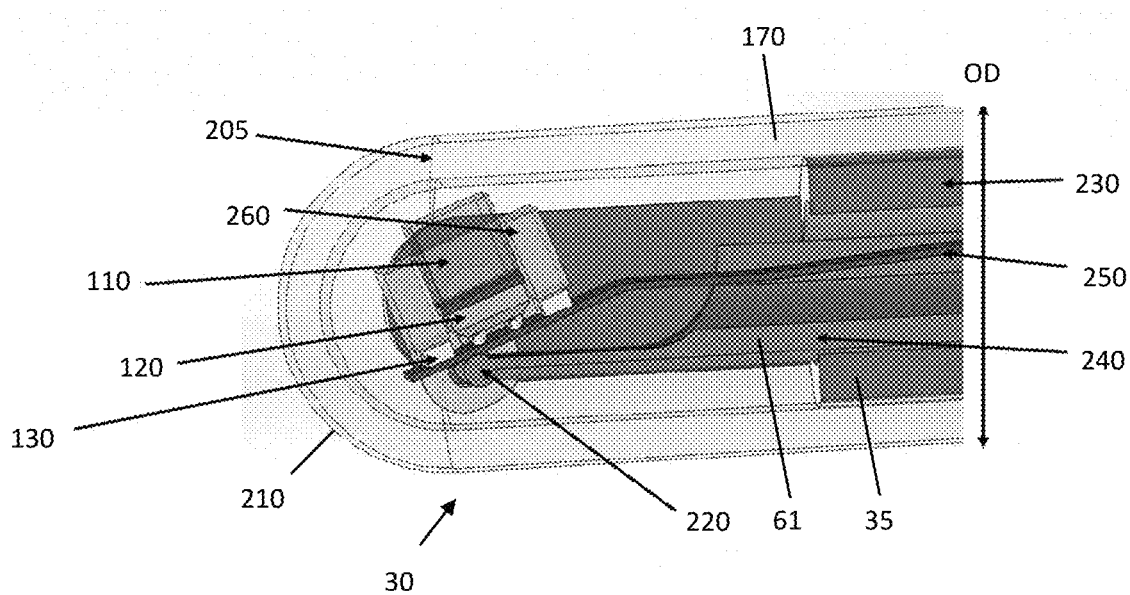
FIG. 6 is a cross-sectional view of a distal end of a multi-angle imaging device, comprising an inner barrel, an outer barrel, and a flexible PCB, in accordance with one embodiment of the disclosure.

FIG. 6 is a cross-sectional view of a distal end of multi-angle imaging device 30, comprising inner barrel 61, outer barrel 35, and flexible printed circuit board 250. Lens system 110 in the illustrated embodiment is seated on top of imager 120. LED lights 130 are seated below light pipe 260. In some embodiments, light pipe 260 and LED lights 130 extend circumferentially about imager 120 and lens system 110. Manipulation of pivot lever 150 toward proximal end 190 moves connecting rod 240 which causes distal movement of angle activator pivot 220, straightening of flexible printed circuit board 250 and adjustment of viewing angle α. In the illustrated embodiment, angle activator pivot 220 is extended distally and imager 120 is positioned such that viewing axis 75 extends through an upper edge 205 of dome cap 210. Cylindrical rotating platform is rotated when pivot handle 140 is rotated by a user. In various embodiments the pivot handle can be directly mechanically linked to the rotating platform, can be linked by gears, by pulleys or can be electronically linked. The outer diameter (OD) of elongate shaft 170 may be, for example, less than 20 mm, less than 10 mm, less than 6 mm, less than 4 mm, less than 3 mm, between 3 mm and 20 mm, between 4 mm and 10 mm, between 4 mm and 6 mm, or between 6 mm and 20 mm.

Figure 7:
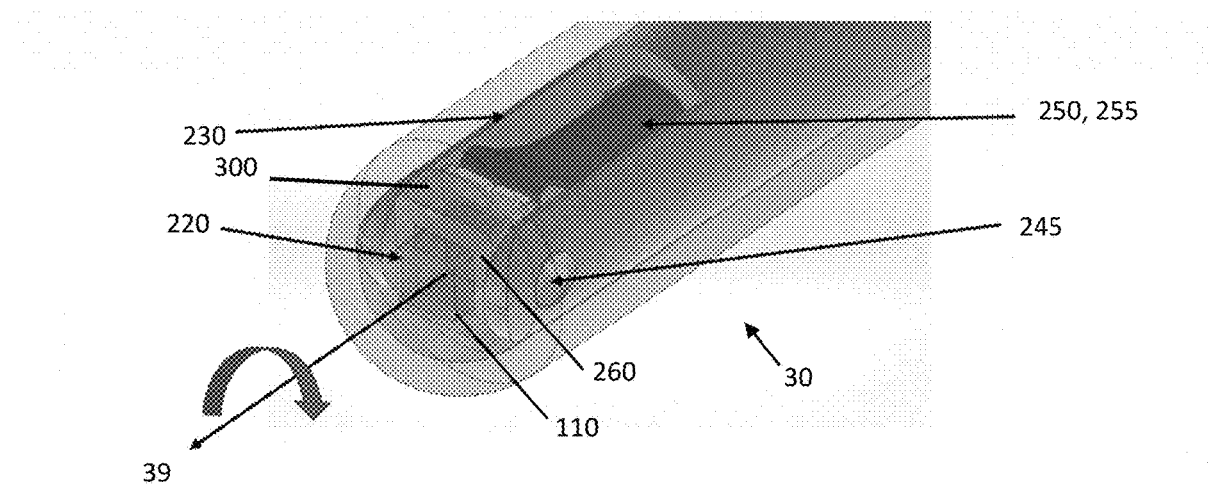
FIG. 7 is a perspective view of a distal end of a multi-angle imaging device, in accordance with one embodiment of the disclosure.

FIG. 7 is a perspective view of a distal end of multi-angle imaging device 30. Multi-angle platform 300 is housed within dome cap 210. In some embodiments, dome cap 210 is transparent, and in some cases can be a low refractive index material. Low refractive index materials can include, for example, transparent fluorinated polymers or glass having a refractive index of less than 1.6, less than 1.55, less than 1.5 or less than 1.45. In some embodiments, a transparent section extends beyond the dome cap such that the camera's view is not obstructed by an opaque outer sleeve. In the illustrated embodiment, the distal end of lens system 110 is square-shaped and light pipe 260 is positioned surrounding lens system 110. Cylindrical rotating platform 230 is manipulated with pivot handle 140 to rotate the imager 120 about barrel axis 39. Multi-angle platform 300 is pivoted about camera module mounting axis 245 by manipulating pivot lever 150. In some embodiments, camera module mounting axis 245 acts as a hinge point for multi-angle platform 30 during manipulation of viewing axis 75.

Figure 8:
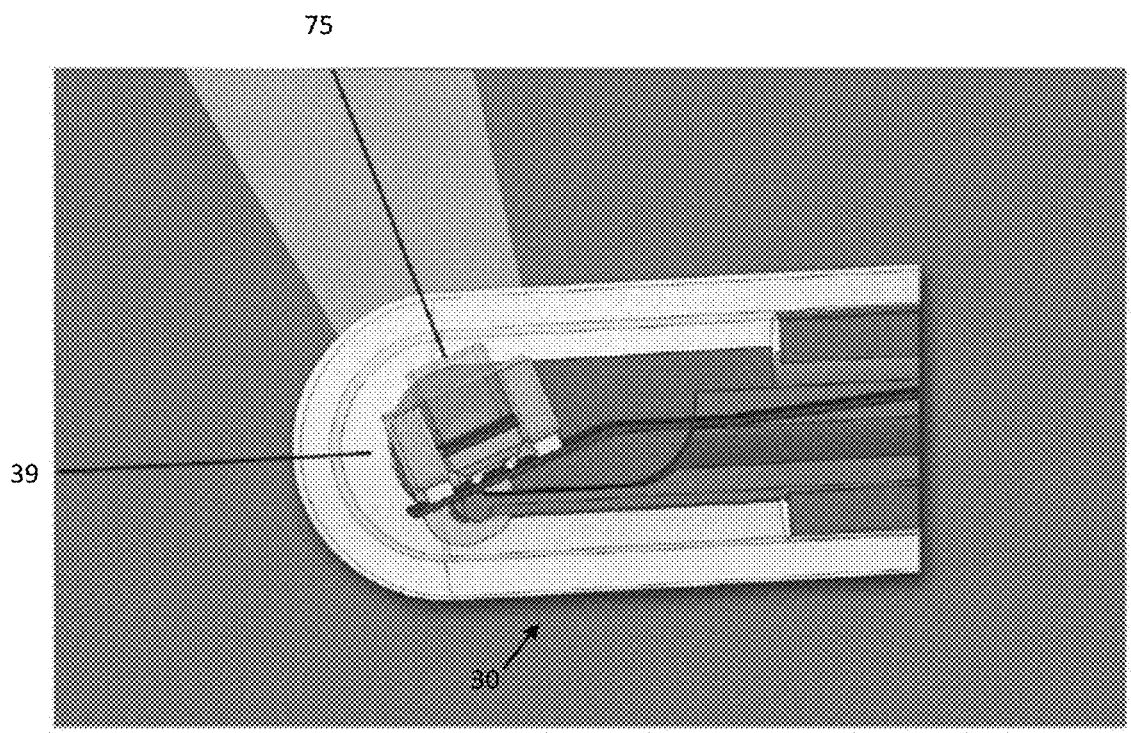
FIG. 8 is a cross-sectional view of a distal end of a multi-angle imaging device, in accordance with one embodiment of the disclosure.
Figure 9A:
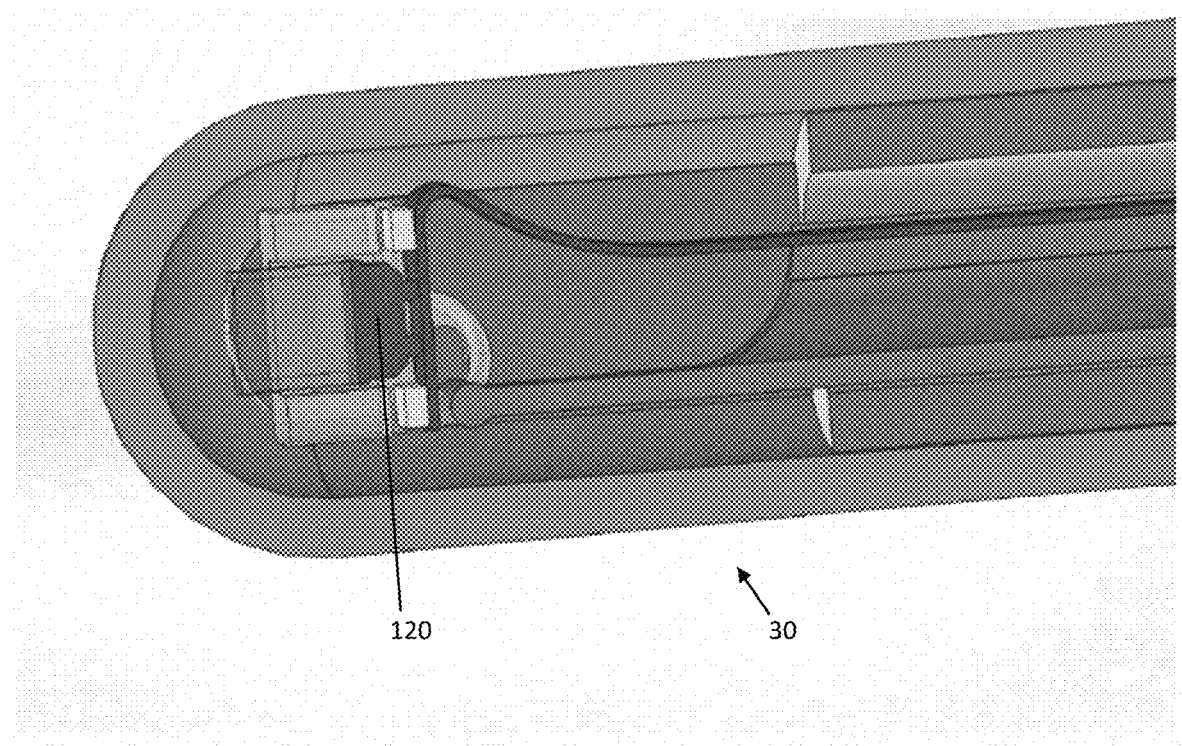
FIG. 9A is a cross-sectional view of a distal end of a multi-angle imaging device, where the imaging device is positioned in line with a longitudinal axis of an elongate shaft (0° from the longitudinal axis), in accordance with one embodiment of the disclosure.
Figure 9B:
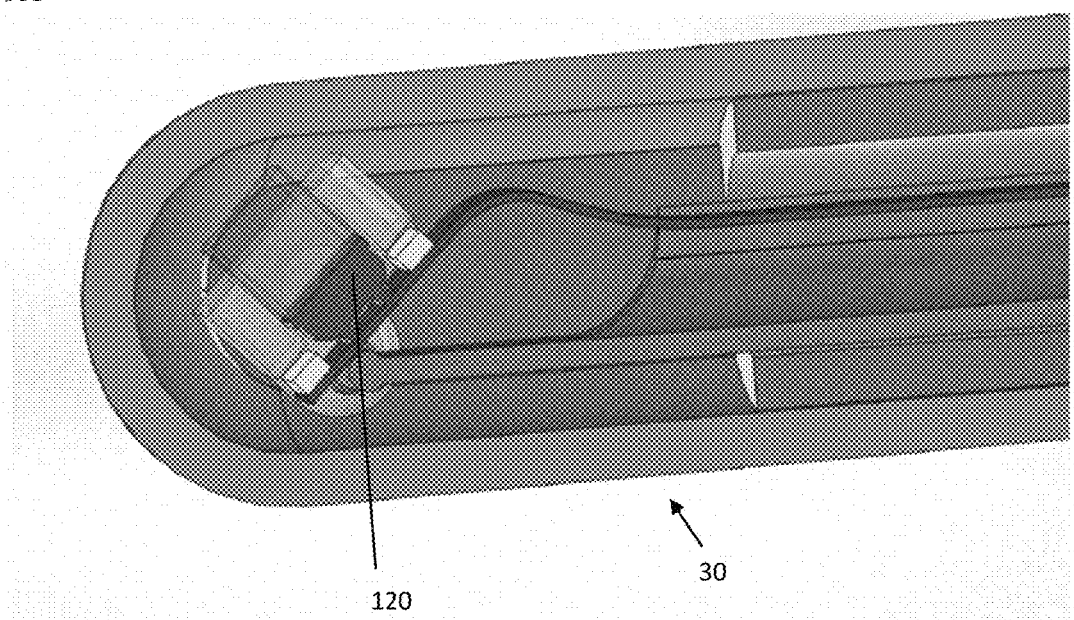
FIG. 9B is a cross-sectional view of a distal end of a multi-angle imaging device, where the imaging device is positioned at a 45° angle with respect to a longitudinal axis of an elongate shaft, in accordance with one embodiment of the disclosure.
Figure 9C:
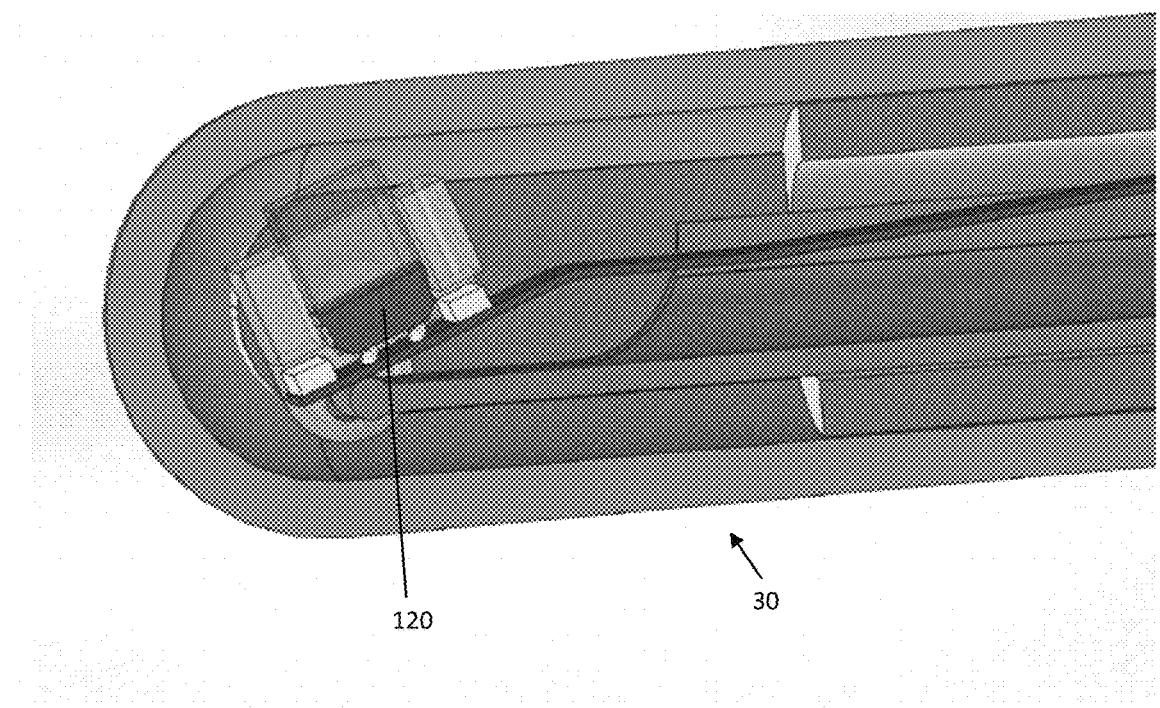
FIG. 9C is a cross-sectional view of a distal end of a multi-angle imaging device, where the imaging device is positioned at a 70° angle with respect to a longitudinal axis of an elongate shaft, in accordance with one embodiment of the disclosure.

FIG. 8 is a cross-sectional view of a distal end of multi-angle imaging device 30 illustrating barrel axis 39 and viewing axis 75.

FIGS. 9A-C and 11A-C illustrate cross-sectional and perspective views, respectively, of a distal end of multi-angle imaging device 30, where imager 120 changes position from being in line with barrel axis 39, to being positioned at about a 45° angle with respect to barrel axis 39, to being positioned at about a 70° angle with respect to barrel axis 39.

Figure 10:
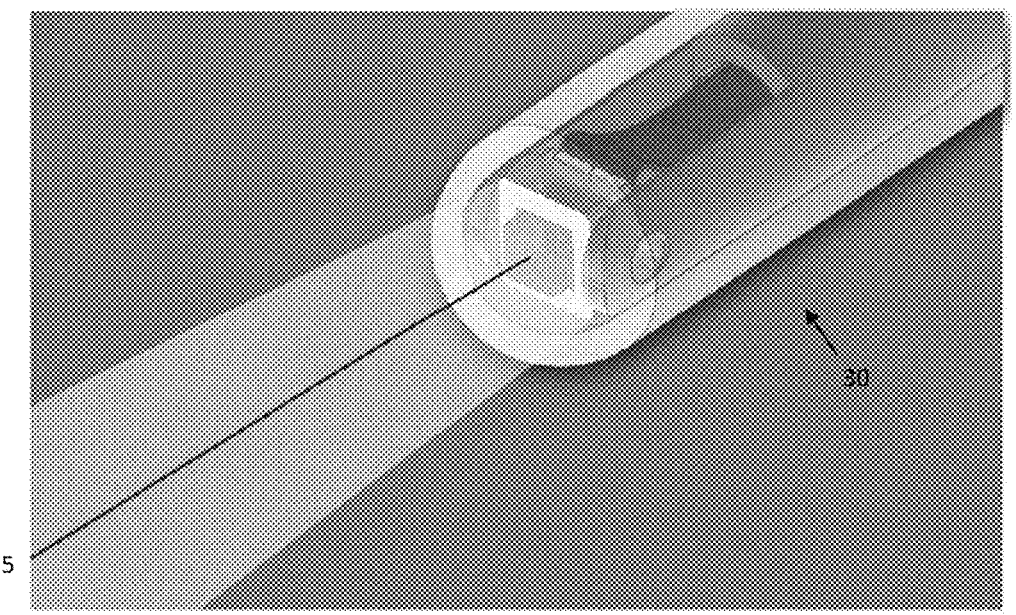
FIG. 10 is a perspective view of a distal end of a multi-angle imaging device, in accordance with one embodiment of the disclosure.
Figure 11A:
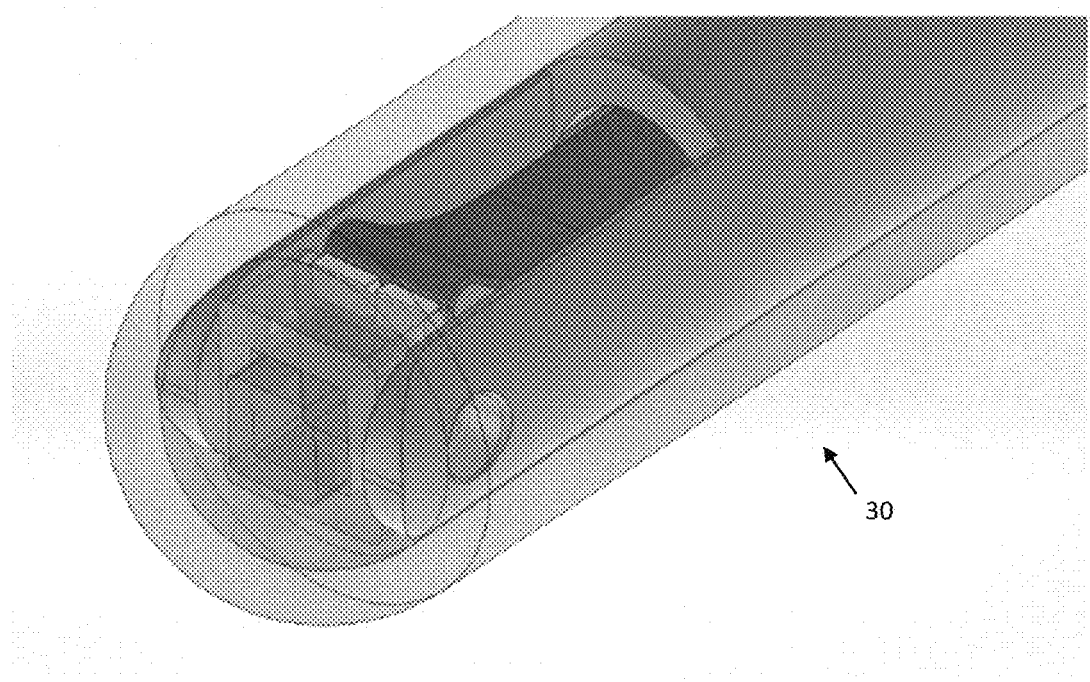
FIG. 11A is a perspective view of a distal end of a multi-angle imaging device, where the imaging device is positioned in line with a longitudinal axis of an elongate shaft (0° from the longitudinal axis), in accordance with one embodiment of the disclosure.
Figure 11B:
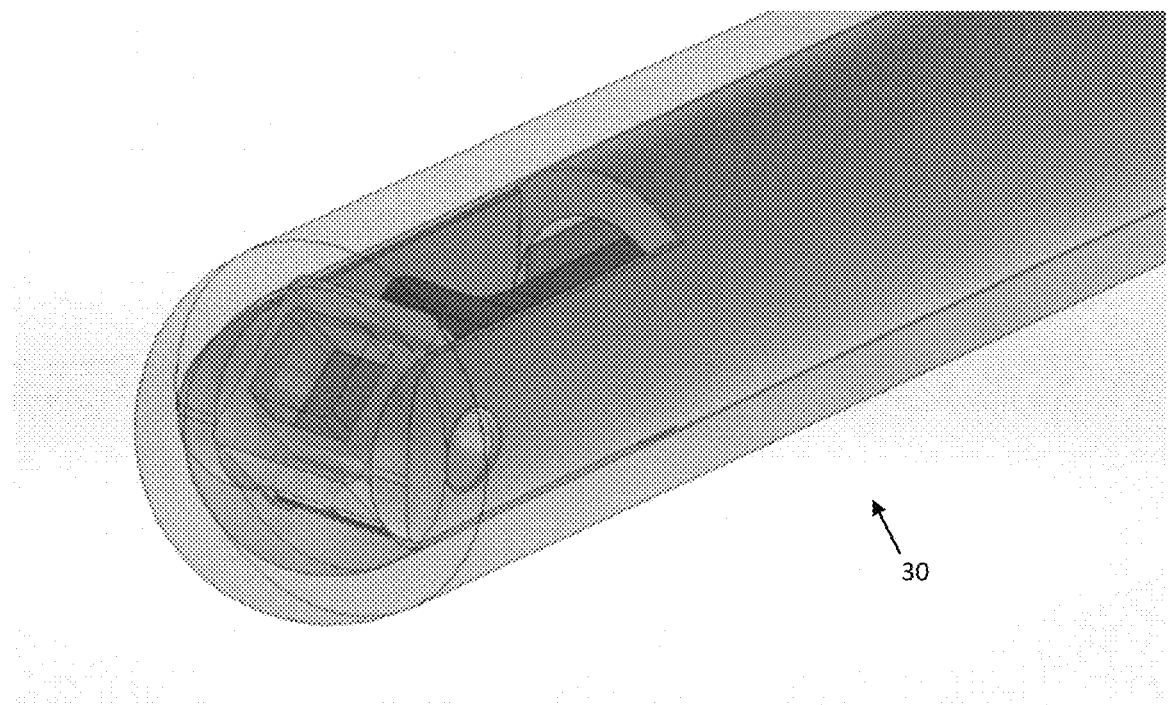
FIG. 11B is a perspective view of a distal end of a multi-angle imaging device, where the imaging device is positioned at a 45° angle with respect to a longitudinal axis of an elongate shaft, in accordance with one embodiment of the disclosure.
Figure 11C:
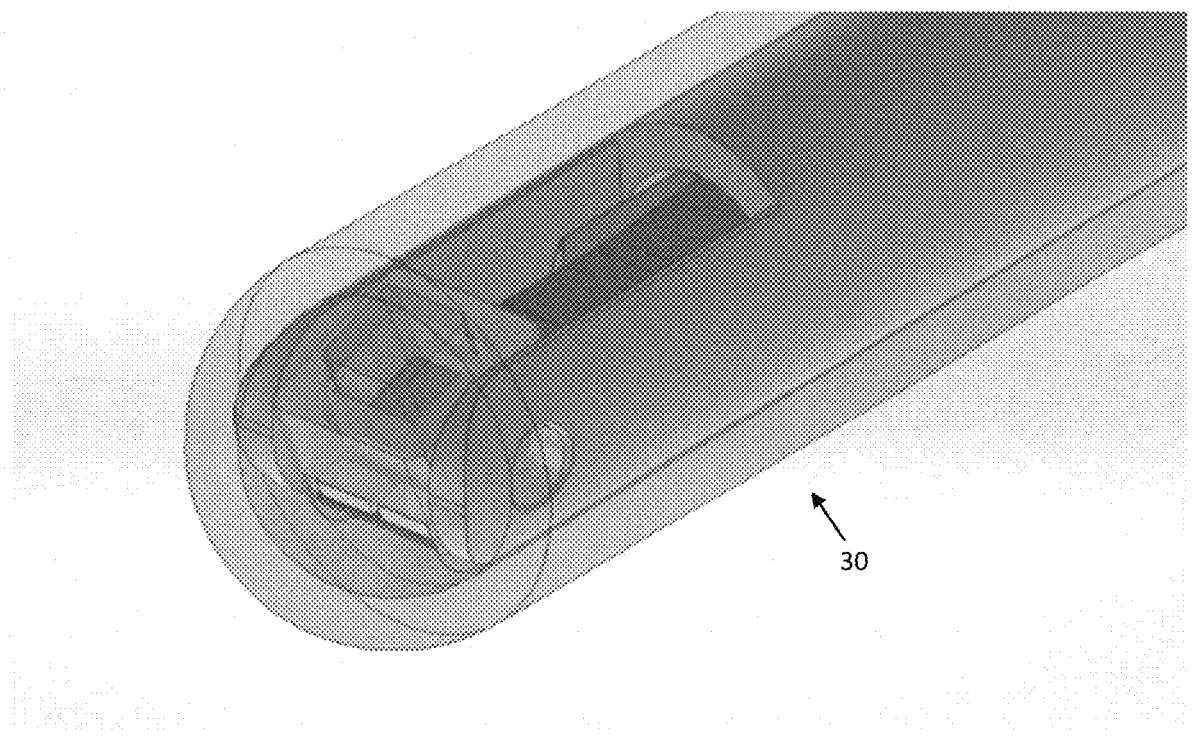
FIG. 11C is a perspective view of a distal end of a multi-angle imaging device, where the imaging device is positioned at a 70° angle with respect to a longitudinal axis of an elongate shaft, in accordance with one embodiment of the disclosure.

FIG. 10 is a perspective view of a distal end of multi-angle imaging device, wherein viewing axis 75 is aligned with barrel axis 39.

Figure 12:
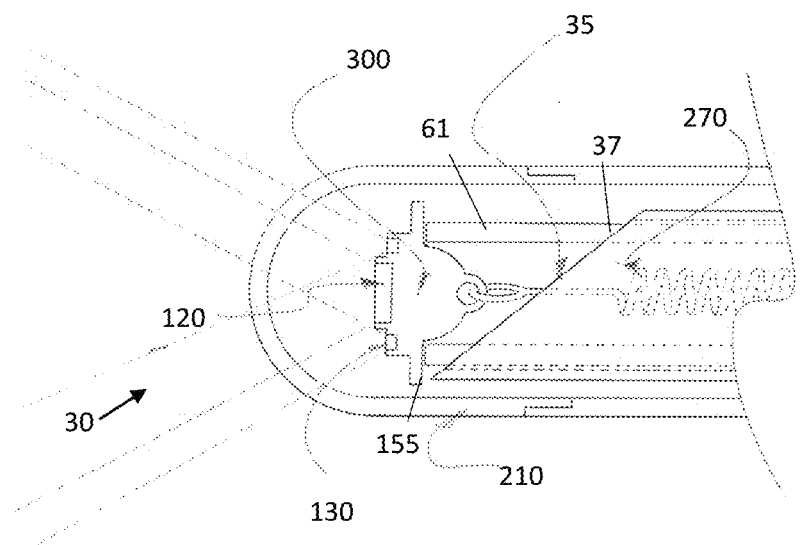
FIG. 12 is a cross-sectional view of a distal end of a multi-angle imaging device, comprising an inner barrel, an outer barrel, and a tensioning spring, in accordance with one embodiment of the disclosure.

FIG. 12 is a cross-sectional view of distal end 90 of multi-angle imaging device 30, comprising inner barrel 61, outer barrel 35, and tensioning spring 270. During manipulation of pivot lever 150, tension is increased on tensioning spring 270 and inner barrel 61 is pulled back into outer barrel 35. As tension is applied, outer lip 155 of multi-angle platform 300 makes contact with skewed surface 37 of outer barrel 35 and the angle of multi-angle platform shifts, thereby adjusting the viewing axis 75. In some embodiments, manipulating pivot lever 150 toward proximal end 190 increases tension in tensioning spring 270. In the illustrated embodiment, imager 120 is positioned centrally on multi-angle platform 300 and LED lights 130 surround imager 120.

Figure 13:
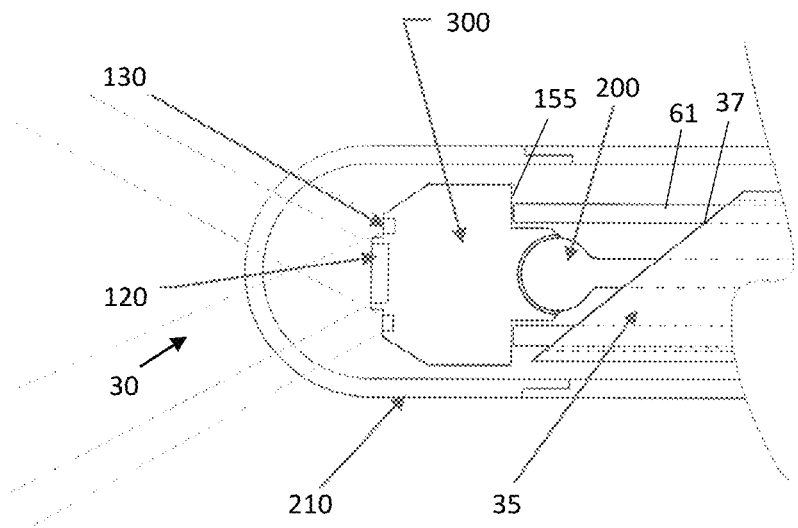
FIG. 13 is a cross-sectional view of a distal end of a multi-angle imaging device, comprising an inner barrel, an outer barrel, and a ball and socket joint, in accordance with one embodiment of the disclosure.

FIG. 13 is a cross-sectional view of a distal end of multi-angle imaging device 30, comprising an inner barrel 61, outer barrel 35, and ball joint 200. During manipulation of pivot lever 150, inner barrel 61 is pulled back into outer barrel 35. As inner barrel 61 is pulled further back into outer barrel 35, outer lip 155 of multi-angle platform 300 makes contact with skewed surface 37 of outer barrel 35 and the angle of multi-angle platform 300 shifts, thereby adjusting viewing axis 75. In the illustrated embodiment, imager 120 is positioned centrally on multi-angle platform 300 and LED lights 130 surround imager 120.

The foregoing description of the embodiments of the disclosure has been presented for the purpose of illustration; it is not intended to be exhaustive or to limit the claims to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed is:

1. A multi-angle imaging device comprising:
   an outer barrel and an inner barrel, the inner barrel being retained in, and rearwardly movable within the outer barrel, the inner barrel and the outer barrel contained within an elongate shaft;
      an imaging device configured to rotate about a longitudinal axis of the elongate shaft by rotating the outer barrel;
      the imaging device operably attached to a distal end of the outer barrel, configured such that rearward movement of the inner barrel with respect to the outer barrel causes movement of the imaging device about a camera module mounting axis that is perpendicular to the axis of the elongate shaft and adjusts a viewing angle of the imaging device;
      an electronic module configured to receive a digital image from the imaging device; and
      a display operatively coupled to the electronic module, the display configured to present the digital image from the imaging device.

2. The multi-angle imaging device of claim 1, further comprising a camera angle activator pivotally connecting a distal end of the inner barrel to the imaging device and configured to control rotation of the imaging device.

3. The multi-angle imaging device of claim 1, wherein the imaging device comprises at least one of a lens system, an imager, a camera imager, and an ultrasound probe.

4. The multi-angle imaging device of claim 1, wherein the elongate shaft is configured with a transparent dome cap at the distal end.

5. The multi-angle imaging device of claim 1, further comprising a light pipe concentrically surrounding the imaging device.

6. The multi-angle imaging device of claim 5, having one or more LED lights positioned proximally to the light pipe to illuminate an area of interest.

7. The multi-angle imaging device of claim 1, wherein the outer barrel comprises a skewed end.

8. The multi-angle imaging device of claim 7 wherein the multi-angle imaging platform comprises an outer lip configured to engage with a skewed end of the outer barrel to cause rotation of the multi-angle imaging platform.

9. The multi-angle imaging device of claim 8, further comprising a handle positioned at a proximal end of the elongate shaft configured with at least one of a pivot lever and a pivot handle.

10. The multi-angle imaging device of claim 9, wherein the pivot lever is configured to urge the inner barrel to extend distally from the outer barrel thereby causing the multi-angle platform to rotate.

11. The multi-angle imaging device of claim 10, wherein the pivot lever is configured with regularly spaced detents.

12. The multi-angle imaging device of claim 9, wherein the pivot handle is configured to cause rotation of the outer barrel about a barrel axis up to at least 360°.

13. A multi-angle imaging device comprising:
   an outer barrel and an inner barrel, the inner barrel being slidably retained in, and rearwardly movable within the outer barrel, the inner barrel and the outer barrel contained within a rigid elongate shaft;
   an imaging device hingedly connected to a distal end of the inner barrel, the imaging device configured to: rotate about a longitudinal axis of the elongate shaft by rotating the outer barrel, move about a camera module mounting axis that is perpendicular to the axis of the elongate shaft when the inner barrel rearwardly moves with respect to the outer barrel, and generate a digital image; and
   a multi-angle platform housing the imaging device, the multi-angle platform comprising an outer lip configured to engage with a skewed end of the outer barrel to cause rotation of the multi-angle platform.

14. The multi-angle imaging device of claim 13, further comprising a flexible printed circuit board (PCB) operably attached to the inner barrel, wherein movement of the inner barrel is configured to cause movement of the flexible printed PCB and rotation of the imaging device.

15. The multi-angle imaging device of claim 13, further comprising a spring housed within the inner barrel.

16. The multi-angle imaging device of claim 13, further comprising a ball joint housed within the inner barrel.

17. The multi-angle imaging device of claim 13, further comprising a handle positioned at a proximal end of the elongate shaft, the handle configured with at least one of a pivot lever and a pivot handle.

18. The multi-angle imaging device of claim 17, wherein the pivot lever is configured to urge the inner barrel to extend distally from the outer barrel thereby causing the multi-angle platform to rotate.

19. The multi-angle imaging device of claim 18, wherein the pivot lever is configured with regularly spaced detents.

20. The multi-angle imaging device of claim 17, wherein the pivot handle is in mechanical communication with the outer barrel and is configured to rotate the outer barrel about a barrel axis up to at least 360°.

\* \* \* \* \*